(12) United States Patent
Qing et al.

(10) Patent No.: US 10,987,065 B2
(45) Date of Patent: Apr. 27, 2021

(54) MEDICAL MONITORING SYSTEM, METHOD OF DISPLAYING MONITORING DATA, AND MONITORING DATA DISPLAY DEVICE

(71) Applicant: SHENZHEN MINDRAY BIO-MEDICAL ELECTRONICS CO., LTD., Shenzhen (CN)

(72) Inventors: Lei Qing, Shenzhen (CN); Qinglin Tao, Shenzhen (CN); Shuaijun Liu, Shenzhen (CN); Yande He, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

(*) Notice: Subject to any disclaimer, the term of this patent is extended or adjusted under 35 U.S.C. 154(b) by 83 days.

(21) Appl. No.: 15/949,909

(22) Filed: Apr. 10, 2018

(65) Prior Publication Data

US 2018/0263575 A1 Sep. 20, 2018

Related U.S. Application Data

(63) Continuation of application No. PCT/CN2015/091666, filed on Oct. 10, 2015.

(51) Int. Cl.
*G06F 3/048* (2013.01)
*A61B 5/00* (2006.01)
(Continued)

(52) U.S. Cl.
CPC .......... *A61B 5/7445* (2013.01); *A61B 5/0006* (2013.01); *A61B 5/0013* (2013.01);
(Continued)

(58) Field of Classification Search
CPC .......... G06F 3/00; G06F 3/048; G06F 3/0481; G06F 3/0484; G06F 3/04847;
(Continued)

(56) References Cited

U.S. PATENT DOCUMENTS

| 8,725,527 | B1* | 5/2014 | Kahn | G16H 10/60 |
| | | | | 705/2 |
| 2006/0013462 | A1* | 1/2006 | Sadikali | G16H 40/63 |
| | | | | 382/132 |

(Continued)

FOREIGN PATENT DOCUMENTS

| CN | 102743156 | 10/2012 |
| CN | 103648372 | 3/2014 |

(Continued)

*Primary Examiner* — Xiomara L Bautista
(74) *Attorney, Agent, or Firm* — Kory D. Christensen

(57) ABSTRACT

A medical intensive care system includes one or more signal sampling devices to detect at least one physiological parameter and parameter data corresponding thereto; memory to store the parameter data, and provide historical parameter data by storing the parameter data in a chronological order; a processor to process the historical parameter data to obtain a plurality types of data in an intensive care time interval; a display to display the plurality types of the data and current parameter data, comparatively, and update, when a historical intensive care time interval is adjusted, the plurality types of the data according to a change in the time interval.

20 Claims, 7 Drawing Sheets

(51) Int. Cl.
  *G01D 7/00* (2006.01)
  *G16Z 99/00* (2019.01)
  *A61B 5/339* (2021.01)
  *A61B 5/0205* (2006.01)
  *A61B 5/021* (2006.01)
  *A61B 5/08* (2006.01)
  *A61B 5/145* (2006.01)
  *A61B 5/1455* (2006.01)

(52) U.S. Cl.
  CPC .............. *A61B 5/339* (2021.01); *A61B 5/743* (2013.01); *G01D 7/00* (2013.01); *G16Z 99/00* (2019.02); *A61B 5/002* (2013.01); *A61B 5/0008* (2013.01); *A61B 5/021* (2013.01); *A61B 5/02055* (2013.01); *A61B 5/0816* (2013.01); *A61B 5/14532* (2013.01); *A61B 5/14551* (2013.01); *A61B 2562/08* (2013.01)

(58) Field of Classification Search
  CPC ...... G06F 19/00; G06F 19/3418; G06T 11/20; A61B 5/00; A61B 5/0006; A61B 5/0008; A61B 5/0013; A61B 5/044; A61B 5/0452; A61B 5/14551; A61B 2562/08; A61B 5/743; A61B 5/7445; G01D 7/04; G16H 15/00
  See application file for complete search history.

(56) References Cited

U.S. PATENT DOCUMENTS

| | | | |
|---|---|---|---|
| 2007/0208263 A1* | 9/2007 | John | A61B 5/0452 600/509 |
| 2008/0058656 A1* | 3/2008 | Costello | A61B 5/1107 600/508 |
| 2009/0054743 A1 | 2/2009 | Stewart | |
| 2009/0131762 A1* | 5/2009 | Pelzek | G04C 13/02 600/301 |
| 2011/0077971 A1* | 3/2011 | Surwit | G06F 19/3418 705/3 |
| 2011/0227739 A1* | 9/2011 | Gilham | G16H 40/63 340/573.1 |
| 2012/0095304 A1* | 4/2012 | Biondi | G16H 50/20 600/301 |
| 2012/0095778 A1* | 4/2012 | Gross | G16H 40/63 705/2 |
| 2013/0044111 A1* | 2/2013 | VanGilder | A61B 5/044 345/440 |
| 2014/0022256 A1 | 1/2014 | Carnes et al. | |
| 2014/0249854 A1* | 9/2014 | Moore | G16H 15/00 705/3 |
| 2014/0275819 A1 | 9/2014 | Kassem | |
| 2015/0097701 A1 | 4/2015 | Al-Ali | |
| 2015/0161331 A1* | 6/2015 | Oleynik | G16H 20/00 705/3 |
| 2015/0234993 A1* | 8/2015 | Detzler | G16H 40/63 702/19 |
| 2016/0267225 A1* | 9/2016 | Aucoin | G06Q 50/24 |
| 2019/0053761 A1* | 2/2019 | Young | A61B 5/4815 |

FOREIGN PATENT DOCUMENTS

| | | |
|---|---|---|
| CN | 104042187 | 9/2014 |
| CN | 104798074 | 7/2015 |

* cited by examiner

| | | | | | | | | | | |
|---|---|---|---|---|---|---|---|---|---|---|
| History | | | | | | | | | | |
| | List Trends | Graphic Trends | Events | Full Disclosure | OxyCRG | 12-lead ECG | ST | | | |
| 05-09 | 19:58:40 | 19:58:45 | 19:58:50 | 19:58:55 | 19:59:00 | 19:59:05 | 19:59:05 | 19:59:10 | 19:59:15 | 19:59:20 |
| HR | 60 | 60 | 60 | 60 | 60 | 60 | 60 | 60 | 60 | 60 |
| SpO2 SpO2b | 98/92 | 98/92 | 98/92 | 98/92 | 98/92 | 98/92 | 98/92 | 98/92 | 98/92 | 98/92 |
| NIBP | 92/98 (60) 19:58 | 92/98 (60) 19:58 | 92/98 (60) 19:58 | 92/98 (60) 19:58 | 92/98 (60) 19:58 | 92/98 (60) 19:58 | --/-- (--) 19:58 | --/-- (--) 19:58 | --/-- (--) 19:58 | --/-- (--) 19:58 |
| RR | 20 | 20 | 20 | 20 | 20 | 20 | 20 | 20 | 20 | 20 |
| PR | 60 | 60 | 60 | 60 | 60 | 60 | 60 | 60 | 60 | 60 |
| Art | 120/75 (90) | 120/75 (90) | 120/75 (90) | 120/75 (90) | 120/75 (90) | 120/75 (90) | 120/75 (90) | 120/75 (90) | 120/75 (90) | 120/75 (90) |
| pArt | 120/75 (90) | 120/75 (90) | 120/75 (90) | 120/75 (90) | 120/75 (90) | 120/75 (90) | 120/75 (90) | 120/75 (90) | 120/75 (90) | 120/75 (90) |
| pCVP | 20 | 20 | 20 | 20 | 20 | 20 | 20 | 20 | 20 | 20 |
| PA | 120/75 (90) | 120/75 (90) | 120/75 (90) | 120/75 (90) | 120/75 (90) | 120/75 (90) | 120/75 (90) | 120/75 (90) | 120/75 (90) | 120/75 (90) |
| PAWP | 20 | 20 | 20 | 20 | 20 | 20 | 20 | 20 | 20 | 20 |
| ICP | 20 | 20 | 20 | 20 | 20 | 20 | 20 | 20 | 20 | 20 |

05-04   05-05   05-06   05-07   05-08   05-09 19:58

Group  Standard ▼   Interval  55 ▼

FIG. 5

MEDICAL MONITORING SYSTEM, METHOD OF DISPLAYING MONITORING DATA, AND MONITORING DATA DISPLAY DEVICE

CROSS-REFERENCE TO RELATED APPLICATIONS

This application is a continuation of PCT Application No. PCT/CN2015/091666, filed Oct. 10, 2015, for MEDICAL INTENSIVE CARE SYSTEM, METHOD OF DISPLAYING INTENSIVE CARE DATA, AND INTENSIVE CARE DATA DISPLAY DEVICE, which is incorporated herein by reference.

TECHNICAL FIELD

The present disclosure relates to the field of medical monitoring systems, and in particular to a medical monitoring system, a method of displaying monitoring data, and a monitoring data display device.

BACKGROUND ART

Patient monitoring systems are commonly used, for example, in intensive care units (ICUs) of hospitals to monitor physiological states of patients. A common patient monitoring system is a bedside monitoring device having one or more sensors disposed on the patient to sense parameter data, such ECG, blood pressure, blood oxygen, blood glucose, and temperature. The parameter data can be displayed on a video display or stored for subsequent analysis.

When health care personnel review historical parameter data of the patient with a monitoring device, they generally need to browse parameter change conditions of the patient over a past period of time so as to find anomalous or key change time points for inspection. Conventional monitoring devices generally present historical data of the patient with one window, and the health care personnel adjust the contents of the historical data of the patient displayed in the window by adjusting a sampling interval or window time interval of the historical data of the patient displayed in the window. A defect of this method is that the health care personnel cannot observe parameter data change conditions of the patient outside the selected time interval of the display window when inspecting with a smaller data sampling interval, e.g., shorter window time interval. Likewise, when inspecting a greater data sampling interval, e.g., longer window time interval, although the health care personnel can observe the parameter data change conditions over a wider time range, information about these anomalous or key change time points is not displayed in sufficient detail, which causes the health care personnel to frequently switch between different data sampling intervals or window time intervals, making browsing operations inconvenient.

SUMMARY

To solve the aforementioned problems, a medical monitoring system, a method of displaying monitoring data, and a monitoring data display device are provided. In one embodiment, a medical monitoring system includes: one or more signal sampling devices to detect at least one physiological parameter and parameter data corresponding thereto; a memory to store the parameter data sampled by the one or more signal sampling devices, and provide historical parameter data by storing the parameter data in a chronological order; a processor to process the historical parameter data to obtain at least two types of data respectively corresponding to the historical parameter data in a same monitoring time interval, and send the at least two types of data and current parameter data to a display; wherein the display is to display the at least two types of data and the current parameter data comparatively, and update, when the monitoring time interval is adjusted, the displayed at least two types of data according to a change in the time interval.

In one embodiment, the method includes: obtaining at least one physiological parameter and parameter data corresponding thereto; providing historical parameter data by storing the parameter data in a chronological order; processing the historical parameter data to obtain at least two types of data respectively corresponding to the historical parameter data in one and the same monitoring time interval; and displaying the at least two types of data and the current parameter data, comparatively, and updating, when the monitoring time interval is adjusted, the at least two types of data according to a change in the time interval.

A monitoring data display device may include: a memory to provide historical parameter data by storing parameter data corresponding to at least one physiological parameter in a chronological order; a processor to process the historical parameter data to obtain at least two types of data in one and the same monitoring time interval, and send the at least two types of data and current parameter data to a display; and the display to display the at least two types of data and the current parameter data comparatively, and update, when the monitoring time interval is adjusted, the displayed at least two types of data according to a change in the time interval.

The disclosed medical monitoring system, method of displaying monitoring data, and monitoring data display device enhance convenience for users, such as health care personnel, in comparing and inspecting parameter data of a patient in a historical monitoring time interval, greatly improving the user experience.

BRIEF DESCRIPTION OF THE DRAWINGS

FIG. 5 is a schematic diagram of a GUI of a historical monitoring time interval of a medical monitoring system according to some embodiments;

DETAILED DESCRIPTION

The medical monitoring system disclosed in the embodiments of the present disclosure is able to continuously present physiological parameter states of a monitored patient in a clear and concise manner, making it convenient for health care personnel to browse and inspect historical physiological parameter data of the patient and quickly handle anomalous events that occur during monitoring.

In various embodiments, the monitoring system has a touch display screen with a graphical user interface (GUI), one or more processors, and a memory including one or more modules, programs or instruction sets for executing multiple functions. These functions may include remote video conferencing, picture/graphic browsing, a pathological database, calendar information, patient file information display, patient directory information display, etc. The modules, programs or instructions for executing the functions may be contained in a computer program product, such as a non-transitory computer readable medium, for execution by one or more processors.

In various embodiments, the monitoring system may be a multi-function monitoring device having a touch screen or touch display screen. A common actual structure (such as the touch display screen) of the above system may support a variety of applications having an intuitive GUI. The above interface control objects may be implemented with computer languages such as Visual Basic (VB) and Java, which may generate graphical objects displayed on the GUI. The graphical objects may include one or a combination of graphics, text, picture, etc.

An application or function utilizing a gesture input of the touch display screen may be used. Alternatively, a hardware input apparatus (e.g., click wheel, keyboard, mouse, and/or joystick) may also be included to execute an operation similar to the above gesture input on the GUI, for example, a cursor is controlled by the hardware input apparatus to move on the GUI to generate an operation action presented on the GUI similar to the gesture input.

An environment in which the various embodiments of the present disclosure may operate is introduced in detail in conjunction with the accompanying drawings. In the following detailed description, many specific details are provided for comprehensive understanding of the embodiments of the present disclosure. However, for those of ordinary skill in the art, it is apparent that the present disclosure may also be implemented without these specific details. In other cases, well-known methods, processes, components, circuits and networks are not described in detail to avoid obscuring the inventive aspects.

Figure 1:
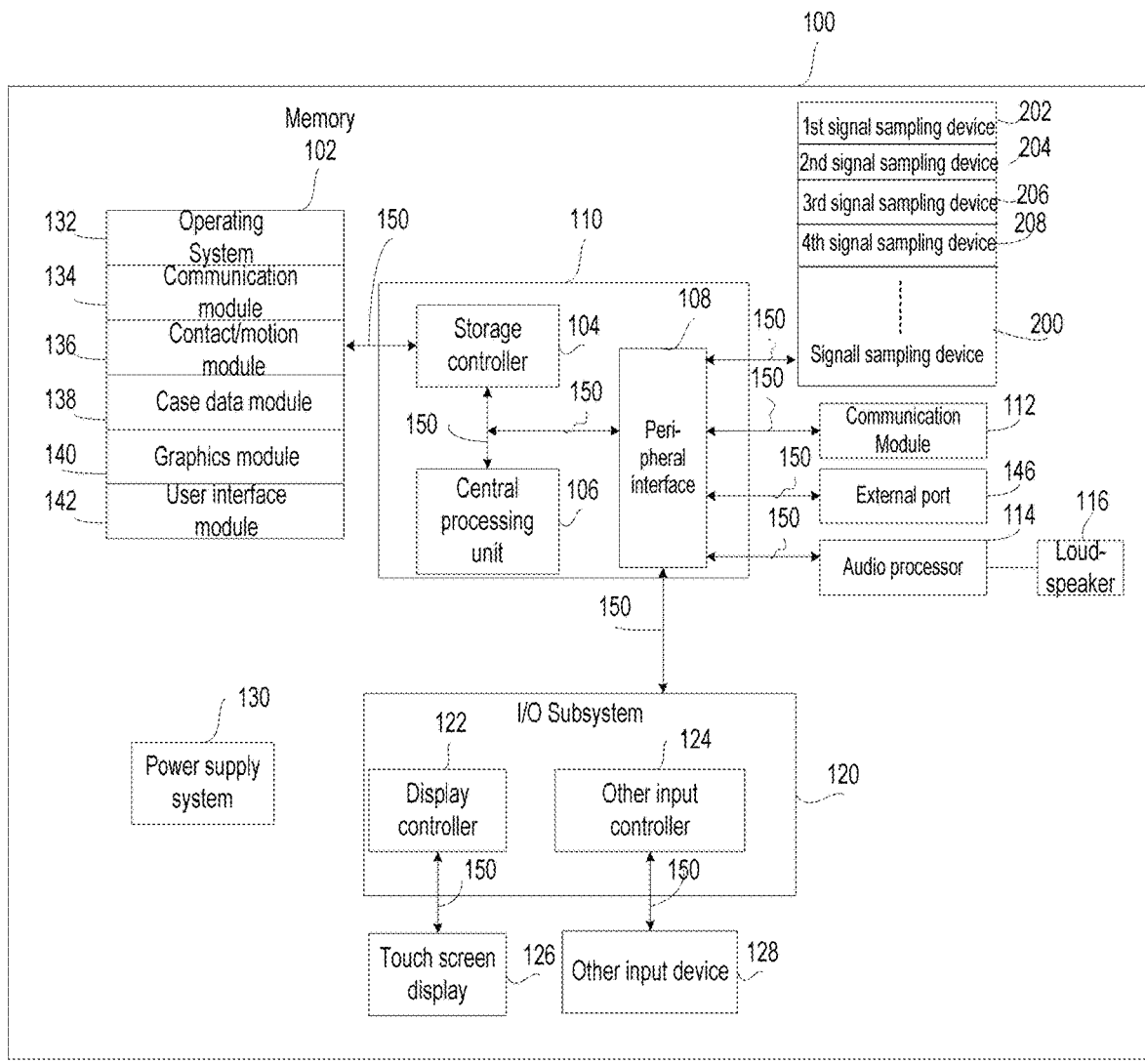
FIG. 1 is a schematic architectural diagram of a medical monitoring system according to some embodiments.

Referring to FIG. 1, a functional structural block diagram is shown of a medical monitoring system 100 with a touch display screen 126. The monitoring system 100 may include a memory 102 including one or more computer readable storage mediums, a storage controller 104, a central processing unit 106 (which may include one or more processors and/or controllers), a peripheral interface 108, an I/O subsystem 120, a display controller 122, a touch display screen 126, other input apparatus controller 124 and other input apparatus 128. The monitoring system 100 may further include a communication module 112, an audio processor 114, a loudspeaker 116, a signal sampling device 200, an external port 146 and a power supply system 130 (including a DC/DC conversion circuit and/or an AC/DC conversion circuit). The above various elements or modules may intercommunicate on one or more communication buses or signal lines 150.

The memory 102 may include a high-speed random access memory, and may also include a non-volatile memory, such as one or more magnetic disk storage devices, flash memory devices, or other non-volatile solid-state storage devices. In some embodiments, the memory 102 may further include storage remote from the one or more processors 106, such as network attached memory accessed via the communication module 112 or the external port 146 and a communication network (not shown), which may include the Internet, one or more internal networks, a local area network (LAN), a wide area network (WAN) and a storage area network (SAN), etc., or an appropriate combination thereof. The storage controller 104 may control the access to the memory 102 from other assemblies such as the CPU 106, the peripheral interface 108 and the like of the monitoring system 100

The peripheral interface 108 couples input and output peripherals connected to the monitoring system 100 with the central processing unit 106. The central processing unit 106 runs or executes various software programs and/or instruction sets stored in the memory 102 so as to execute various functions and applications of the monitoring system 100 and process data.

In various embodiments of the present disclosure, the peripheral interface 108, the central processing unit (CPU) 106 and the storage controller 104 may be implemented, for example, on a single chip 110. In some embodiments, they may also be implemented on a plurality of separate chips.

The communication module 112 is configured to receive a communication signal, convert the same into an electrical signal and convert the electrical signal into a communication signal to transmit. The communication module 112 may be implemented using known techniques and enables the monitoring system 100 to communicate with an external network or other external apparatus. For example, the communication module 112 can connect to the Internet and Intranet of the World Wide Web (WWW) and/or a wireless and/or wired network such as a cellular telephone network, a local area network (LAN) and/or a metropolitan area network (MAN) to communicate with other systems and devices. The communication module 112 can use any one of a variety of communication standards, protocols and techniques, including but not limited to utilizing a wired or wireless medium, including Bluetooth, Ethernet, 802.11(x), a body area network or other wireless protocols.

The audio processor 114 and the loudspeaker 116 provide an audio interface between users (health personnel) and the monitoring system 100. The audio processor 114 may receive audio data from the peripheral interface 108, convert the audio data into an electrical signal, and send the electrical signal to the loudspeaker 116. The loudspeaker 116 converts the electrical signal into sound waves which may be heard by humans. The peripheral interface 108 may retrieve audio data from the memory 102 and/or the communication module 112 and/or send audio data to the memory 102 and/or the communication module 112.

The I/O subsystem 120 couples the touch display screen 126 and the other input apparatus 128 with the peripheral interface 108. The I/O subsystem 120 may include the display controller 122 and one or more other input controllers 124 to control the other input apparatus 128. The one or more other input controllers 124 receive/send an electrical signal from/to the other input apparatus 128. The other input apparatus 128 may include an actual button and a similar apparatus, a drive plate, a slide switch, a joystick, a click wheel, etc. In some embodiments of the present disclosure, the one or more other input controllers 128 may be coupled with any one or more apparatus of a keyboard, an infrared port, a USB port and a mouse, for example.

The touch display screen 126 provides a gesture input interface between the monitoring system 100 and the user, wherein the gesture input interface is implemented mainly by means of a GUI object of a virtual button, soft keyboard, etc. provided on the GUI of the touch display screen 126. The display controller 122 sends an electrical signal to the touch display screen 126 and/or receives an electrical signal from the touch display screen 126. The touch display screen 126 displays a visualized output to the user. The visualized output may include one or a combination of more of a graphic, text, an icon, a picture, etc., which are collectively referred to as a "graphic" herein.

The touch display screen 126 has at least one touch-sensitive surface to receive a gesture input from the user according to touch and/or contact. The display controller 122 calls a relevant module and/or instruction set in the memory 200 to provide a GUI by displaying graphics on the touch display screen 126, detects a gesture input from the user sensed by the touch-sensitive surface, and converts the detected gesture input into a GUI object (such as one or more soft keys, icons or buttons) displayed on the touch display screen 126, so as to realize interaction between the touch display screen 126 and the user. In one embodiment of the present disclosure, the contact operation position between the touch display screen 126 and the user corresponds to the contact position of a direct contact between an input object, such as a user finger, and the touch display screen 126, or a mapping position of the spatial position when the input object, such as a user finger, approaches the touch display screen 126 mapped onto the touch display screen 126.

The touch display screen 126 may use an LCD (liquid crystal display) technique or LPD (luminescent polymer display) technique, but may also use other display techniques, for example, an OLED display, in other embodiments. The display screen in the touch display screen 126 and the display controller 122 may utilize any one of a variety of touch sensing techniques which are currently known or will be developed in the future to detect the contact in the gesture input and any motion or interruption thereof, these touch sensing technique including but not limited to capacitance, resistance, infrared, surface acoustic wave techniques, image recognition-based or data glove-based gesture input techniques, and a sensor array or other elements for determining the proximity between the input object and one or more contact points on the surface of the touch display screen 126.

The monitoring system 100 further comprises a power supply system 130 for providing a power input for various elements or modules or circuits, which includes a power management system, one or more power sources (such as a battery and alternating current (AC)), a charging system, a power failure detection circuit, a power converter or inverter, a power state indicator (for example, a light emitting diode (LED)), and any other components relevant to the generation, management and distribution of power in the monitoring system 100. According to different power sources, the power supply system may contain a DC/DC conversion circuit, or contain an AC/DC conversion circuit.

The monitoring system 100 may further include a signal sampling device 200, and the signal sampling device 200 detects at least one physiological parameter related to a monitored object and acquires parameter data corresponding to the at least one physiological parameter. The at least one piece of physiological parameter data (biological information) related to the monitored object may be multi-monitoring parameter data (information) related to the electrocardiogram (ECG), non-invasive blood pressure (NIBP), heart rate (HR), oxyhemoglobin saturation (SpO2), end-tidal carbon dioxide concentration (EtCO2), body temperature, cardiac output (CO), pulse rate and anesthetic gas analysis, etc. The signal sampling device 200 includes one or more one or more signal sampling devices related to the above plurality pieces of physiological parameter data (information). FIG. 1 shows a signal sampling device 202 to sample an electrocardiogram signal, a second signal sampling device 204 to sample a blood pressure signal, a third signal sampling device 206 to sample the pulse rate, and a fourth signal sampling device 208 to measure the body temperature, etc. which are coupled with the peripheral interface 108. In this embodiment, the signal sampling device 200 includes sensors for directly sampling signals corresponding to physiological parameters and a signal processor to process the signals sampled by the sensors. In addition to the parameter data measured via the signal sampling device 200, patient information further includes any or all information in the case, including but not limited to statistical information, such as the patient's name, bed number, patient identification number (ID) or the ID of the doctor in charge of the patient. The patient information may include the height, weight, family medical history, laboratory reports, etc.

In some embodiments, the memory 102 includes an operating system 132, a communication module (or instruction set) 134, a contact/motion module (instruction set) 136, a case data module (or instruction set) 138, a graphics module (or instruction set) 140 and a user interface display module 142.

The operating system 132 (such as Linux, Unix, OS, Windows or an embedded system like VxWorks) includes various software components and/or drivers which are to control and associate conventional system tasks (such as memory association, storage device control, power supply management, etc.) and facilitate communication between various software and hardware.

The communication module 134 is helpful to communicate with other apparatuses via one or more external ports 146, and further comprises various software modules to process data received by the external port(s) 146. The external port 146 (such as a universal serial bus (USB), FireWire, etc.) is appropriate for being directly or indirectly via a network (such as the Internet, a wireless LAN, etc.) coupled with other apparatus.

The contact/motion module 136 and the touch screen display controller 122 together detect the contact with the touch screen 126. The contact/motion module 136 includes various software components to execute various operations associated with contact detection with the touch screen 126, the operations, for example, including determining whether there is a contact, determining whether the contact is moving, and tracking the movement on the touch screen 126 and determining whether the contact is interrupted (i.e. whether the contact is stopped). The operation of determining the movement of a contact point may include determining the rate (amplitude), velocity (amplitude and direction) and/or acceleration (including the amplitude and/or direction) of the contact point. In some embodiments, the contact/motion module 136 and the touch screen display controller 122 may be implemented using the same module or device.

The graphics module 140 includes various known software components to present and display graphics on the touch screen 126. As used herein, "graphic" may include any object that may be displayed to a user, including but not limited to text, icons (for example, a user interface object including a software key), digital images, waveforms, numerical values, etc.

In some embodiments, the user interface module 142 controls the display of a GUI of the monitoring system 100. When the user interface module 142 or another module or device detects one or more instructions satisfying any one condition for GUI display, then the corresponding graphical interface is switched to for display. More details related to the GUI will be described hereinafter.

FIG. 1 above only refers to a structural block diagram of a medical monitoring system 100, and the monitoring system 100 is merely an example of a type of medical monitoring equipment. The monitoring system 100 above may also have more or fewer elements or modules than FIG. 1, and may also use two or more elements or modules above in combination, or may also perform arrangement of different configurations on the architecture in FIG. 1. The various elements or modules shown in FIG. 1 may be implemented in the form of hardware, software, or a combination of hardware and software, including one or more signal processing and/or application-specific integrated circuits (ASICs).

The monitoring system 100 above may remotely display and inspect medical data obtained by medical detection equipment, for example, the medical data herein may include any one piece of data that may be selected according to user requirements of medical image data, detection data obtained by various detection instruments (such as a blood pressure monitoring result, an electrocardiogram detection result) and configuration parameters corresponding to various detection instruments, etc. With regard to the medical image data, the functions of video playing, picture viewing, image editing (image editing such as commenting, classifying, cutting, pixel adjusting, etc.), video editing (video processing such as remarking, noise removing, video length adjusting, playing effect adjusting, etc.) and medical image data transmission, etc. may be remotely performed by the monitoring system 100 above. The monitoring system 100 above may further remotely control medical detection equipment, for example, receive medical image data and control information fed back by the medical detection equipment via the communication module 112, and/or send a control instruction to the medical detection equipment. The above medical detection equipment may be any one medical detection equipment that may obtain organism image data or sample medical parameter data, such as magnetic resonance imaging (MRI) equipment, ultrasound detection equipment, a blood sample detection instrument, etc.

The monitoring system 100 may have a plurality of GUI states. The GUI states are states that the monitoring system 100 responds to a user's input in a predetermined manner. In some embodiments, the plurality of GUIs include a display interface to display various types of data and current monitoring data in a same monitoring time interval (or period) obtained by the central processing unit 106. In some embodiments of the present disclosure, the various types of data may include a holographic waveform (full disclosure), a parameter graphic trend, a list trend, an anomalous event, respiratory oxygenation, a 12-ECG, and/or an ST segment.

Figure 2:
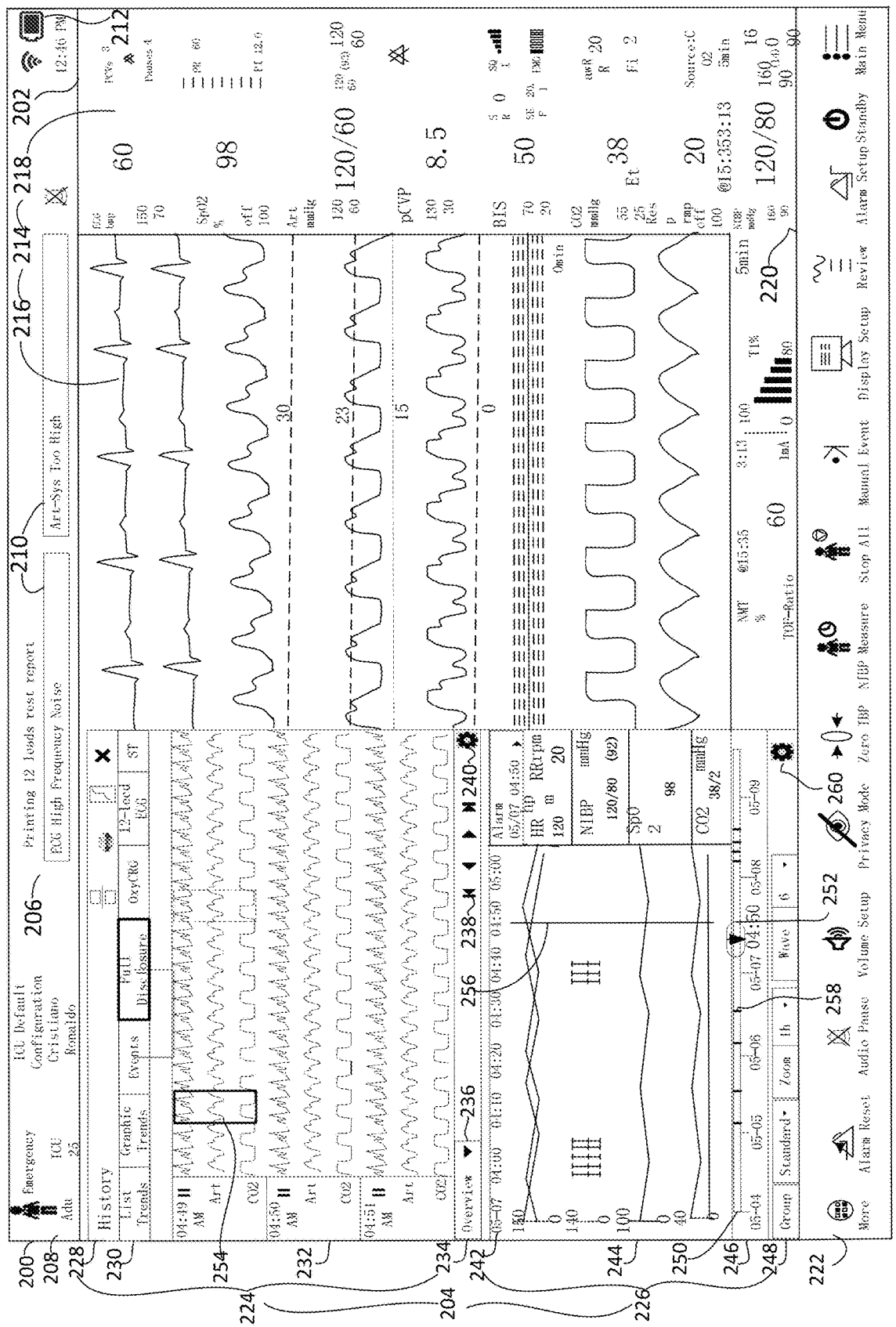
FIG. 2 is a schematic diagram of a graphical user interface (GUI) of a medical monitoring system according to some embodiments.

FIG. 2 is a schematic diagram of a GUI of some embodiments of the present disclosure. The GUI 200 shown in FIG. 2 includes current monitoring data and various types of historical data. In some embodiments, according to an input instruction of a user, the display region of the touch screen 126 is divided into multiple regions, or a plurality of floating windows are displayed on the display region of the touch screen 126. In some embodiments, the number of display regions is at least three, wherein one display region is to display the current parameter data, and the other display regions are to comparatively display various types of historical data in a same period. It should be understand that only a portion of the historical data in each region may relate to the same period. For instance, some regions may include more or less historical data than other regions. However, at least a portion of the historical data in each region should relate to the same time period to facilitate comparison. In some embodiments, these display regions are arranged on the display screen in a tiled manner.

In some embodiments, the number of floating windows is at least two, wherein one floating window is to display the current parameter data, and the other floating window(s) is/are to comparatively display the various types of historical data. Furthermore, in some embodiments, multiple floating windows are arranged on the display screen in a superposed or tiled manner.

In some embodiments, the display regions or floating windows which comparatively display various types of historical data are chronologically associated, that is, the various types of history data displayed are all updated according to a period selected. Thus, if a new time period is selected, the time period for each of the display regions or floating windows is automatically updated.

In some embodiment, data types comparatively displayed in the display regions or floating windows are selected via a configuration icon/button or a setup icon.

In some embodiments, as shown in FIG. 2, the GUI 200 includes: a first floating window 202 and a second floating window 204. In this embodiment, the second floating window 204 is displayed on the left and in front of the first floating window 202 in a superposed manner. The second floating window 204 covers some relatively unimportant waveform information displayed on the left part in the first floating window 202, and real-time monitoring data information on the right part is highlighted. In addition, the display position of the second window 204 may also move according to user requirements. In some embodiments, the first floating window 202 and the second floating window 204 may also be displayed in a tiled manner, which is not limited to the description in the above embodiments.

In some embodiments, the first floating window 202 is to display current parameter data. In this embodiment, the first floating window includes a title region 206, a waveform/data display region 214 and a menu configuration region 220. In some embodiments, the title region 206 is located at the top of the first floating window 202, and may be a long strip-shaped region. The waveform/data display region 214 is distributed in the middle of the first floating window 202. The menu configuration region 210 is located at the bottom of the first floating window 202, and may be a long strip-shaped region.

In some embodiments, the title region 206 includes a patient information region 208, e.g., the number of the ICU where a patient is located, an anomaly label region for important physiological parameters 210, and a current monitoring time region 212. In some embodiments, the anomaly label region for important physiological parameters 210 further includes a button for printing a 12-lead electrocardiogram and an important physiological parameter sampling anomaly label, and the important physiological parameter sampling anomaly label includes but is not limited to ECG high-frequency noise and too high systolic pressure (Art Sys Too High). The current monitoring time region 212 further includes whether to turn on a sound identifier, a current monitoring time interval, a network connection state and an electric quantity identifier of the monitoring system 100, etc.

In some embodiments, the waveform/data display region 214 is distributed in the middle of the first floating window 202. The waveform/data display region 214 correspondingly displays parameter data of the current monitoring time interval. The parameter data is represented in the form of graphics and numerical values. In some embodiments, the waveform/data display region 214 further includes a parameter data region 216 displayed in waveforms and a parameter data region 218 displayed in the form of numerical values. There may also be other forms of the arrangement of graphics and numerical values within the scope of the disclosure. The parameter data region 216 displayed in waveforms may continuously display waveform data including the current monitoring time point and a monitoring time clip prior to same. The monitoring time interval may, for example, be 10 s, and the length of the monitoring time clip may be specifically set up according to parameters of the waveform display frequency and speed, etc.

In some embodiments, the menu configuration region 220 includes at least one menu icon or button 222. The display form of the GUI 200 may be configured via at least one menu icon or button 222. For example, the menu icon or button 222 includes a main menu (Main Menu) button, a privacy mode (Privacy Mode) button, a standby mode (Standby) button, an audio pause (Audio Pause) button and a volume setup (Volume Setup) button, etc.

In some embodiments, the second floating window 204 includes a first part 224 and a second part 226 displayed and arranged side by side in a vertical direction. The first part 224 and the second part 226 respectively and comparatively display a first type of data and a second type of data in a similar monitoring time interval. In this embodiment, the first type of data and the second type of data are any two of a holographic waveform (full disclosure), a parameter graphic trend, a list trend, an anomalous event, respiratory oxygenation, a 12-ECG and an ST segment.

In some embodiment, the first part 224 includes a title bar 228, a menu bar 230, a waveform/data display region 232 and a function region 234. In this embodiment, the title bar 228 is located at the top of the first part, and may be in the shape of a long strip. The title bar 228 is to identify various types of historical data displayed corresponding to the floating window in a historical (History) monitoring time interval.

In some embodiments, the menu bar 230 includes a data type icon or button, the data type icon or button including a list trend (List Trend) button, a graphic trend (Graphic Trend) button, an event (Events) button, a holographic waveform (Full Disclosure) button, a respiratory oxygenation (OxyCRG) button, a 12-lead ECG button and an ST segment (a segment of electric equilibrium phenomenon from the S wave to the starting of the T wave) button. A type of data displayed corresponding to the waveform/data display region 232 may be selected by means of the above data type icon or button. In this embodiment, parameter data in a monitoring time interval are displayed in a holographic waveform (Full Disclosure), which may show all detected real-time waveforms and parameters. In some embodiments, the type of the parameter data further includes a parameter graphic trend, a list trend, an anomalous event, respiratory oxygenation, a 12-ECG and an ST segment, etc. The display form of other types of parameter data will be illustrated in FIGS. 4 to 7.

In some embodiments, the function region 234 includes a data selection pull-down menu 236, a data selection icon 238 and a setup icon 240. The display form of the second window 204 may be selected via the data selection pull-down menu 236. In this embodiment, the display form is a comparison and review (Overview) form. In some embodiments, the type of data displayed in the waveform/data display region 232 may be selected via the data selection icon 238. For example, at present, the parameter data in the monitoring time interval is displayed in the holographic waveform (Full Disclosure). When a first button is clicked, then the type of data of respiratory oxygenation (OxyCRG) may be chosen to be displayed on the waveform/data display region 232, and when second button is clicked, then the waveform/data display region 232 directly jumps and displays the ST segment type of data. In some embodiments, the waveform/data display region 232 may also be configured via the setup icon 240.

In some embodiments, the second part 226 is to comparatively display another type of parameter data in synchronization with the first part 224. In this embodiment, the synchronization refers to the fact that when the monitoring time interval of the first part 224 changes, the monitoring time interval of the second part 226 also updates to the same monitoring time interval as that of the first part 224. In this embodiment, the second part 226 displays parameter data in the same monitoring time interval as the first part 224 in the form of a graphic trend (Graphic Trend).

In some embodiments, the second part 226 includes a monitoring time clip region 242, a data display region 244, a historical monitoring time region 246 and a data configuration region 248.

In some embodiments, the historical monitoring time region 246 includes a timeline 250, and the timeline 250 indicates a whole-time length of the historical data available for inspecting. The timeline 250 may further be provided in the first window 202 or the first part 224 to select a historical monitoring period.

In some embodiments, the inspecting label 252 is displayed as a slide bar/slide block which is sleeved on the timeline 250 and may slide along the timeline 250. The inspecting period is selected by moving the inspecting label 252. When the inspecting period changes, data displayed on the first part 224 and the second part 226 is correspondingly updated to the inspecting period corresponding to the inspecting label 252.

In some embodiments, the timeline 250 is displayed as a horizontal long strip, and the width of the inspecting label 252 is greater than that of the timeline 250. In this way, when users (health care personnel) touch the touch display screen 126 with a finger, the monitoring period is selected more conveniently. The downward arrow of the inspecting label 252 may represent a middle monitoring time point of the inspecting period. The inspecting period represented by the inspecting label 252 would expand in proportion to the length of the inspecting label 252, and the position of the inspecting label 252 corresponds to the monitoring time point in the historical data. An inspecting time represented by a time window 254 of the waveform/data display region 232 is related to an inspecting time represented by a vertical timeline 256 of the data display region 244. With the movement of the time frame 254, the vertical timeline 256 may move accordingly. Of course, with the movement of the vertical timeline 256, the time frame 254 may move accordingly too. A users (monitoring personnel) may utilize his or her finger on the touch display screen 126 or the other input apparatus 128, for example but not limited to a mouse, a handle, a keyboard, a joystick, a click wheel, etc. to control the inspecting label 252, so as to adjust the displayed historical monitoring period.

In some embodiments, the length of the slide bar/slide block shown by the inspecting label 252 may stretch out (expand) and draw back (contract), for example, the slide bar/slide block may be stretched out and drawn back via the relative movement of two contact points detected on the touch display screen 126. The length of the period corresponding to the inspecting label 252 may be expanded by sliding the slide bar/slide block displayed on the touch screen 126 away from each other using two fingers to the left and the right respectively. Likewise, the length of the period corresponding to the inspecting label 252 may be shortened by sliding the slide bar/slide block displayed on the touch screen 126 toward each other using two fingers to the left and the right respectively.

In some embodiments, one or more anomalies identifier 258 for representing an anomalous event is displayed on the timeline 250. The anomalies identifier 258 may be displayed in different colors and shapes according to different long time attributes, and the anomalous events may include a physiological parameter warning, a manually labeled event when health care personnel find an anomaly, and a technical warning event relevant to patient parameter measurement, etc. In some embodiments, according to different attributes of anomalous events above, the anomalies identifier 258 may be displayed as light strips in different colors and/or shapes. For example, anomalies identifiers of different attributes may be displayed as different colors, and the durations of the anomalous events with different attributes may be displayed in different shapes. In this embodiment, the length of the light strip is set according to the length of the duration of an anomalous event. For example, the longer the duration of an anomalous event is, the longer the vertical strip is. Of course, the anomalies identifier 258 may also be set in other shapes according to different attributes of the anomalous events.

Figure 3:
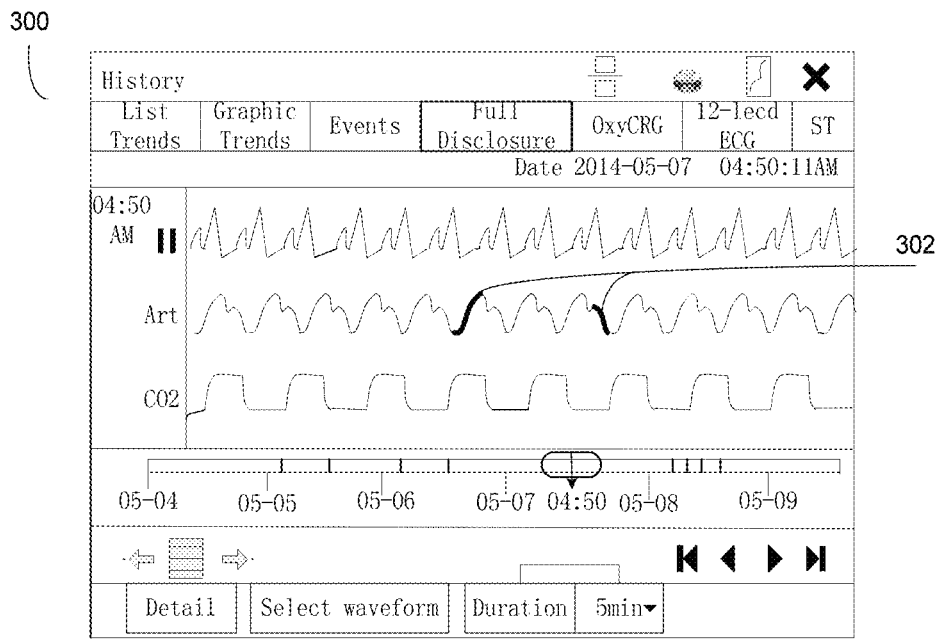
FIG. 3 is a schematic diagram of a GUI of a historical monitoring time interval of a medical monitoring system according to some embodiments.

In some embodiments, the color of each time point on the timeline 250 may indicate the change of a parameter trend value. For example, when the parameter data value changes from a low magnitude to a high magnitude, the color changes from green to red (not shown in the figure). In some embodiments, as shown in FIG. 3, the parameter data corresponding to the anomalies identifier 258 is displayed in different shapes and colors on the parameter trend line. In this embodiment, the parameter data corresponding to the anomalies identifier 258 is displayed in different colors on the parameter trend line, as indicated by 302. In some embodiments, the time point of the inspecting label 252 is displayed in the upper right corner region of the second part 226.

In some embodiments, the second part 226 further includes a data configuration region 248. The data configuration region 248 includes a group (Group) icon or button, an inspecting period menu and a waveform display button. The group (Group) icon or button represents a combination mode of different parameter data in the graphic trend, and is a standard display mode (Standard) in this embodiment. The inspecting period menu includes the length of the displayed monitoring period, i.e. the inspecting period length displayed in the monitoring period region 242. The length of the inspecting period may be configured as several minutes, a few hours, a day or a week, etc. The waveform display button represents the number of waveforms of different parameters which may be displayed at the same time in the graphic trend. The waveform configuration may be set up via the data configuration region 248, and may also be configured via the configuration icon 260.

In some embodiments, the data types displayed in the first part 224 and the second part 226 may be a combination of any two of a full disclosure, a parameter graphic trend, a list trend, an anomalous event, respiratory oxygenation, 12-ECG, an ST segment, etc. Of course, the data types displayed is not limited to the above embodiments. The users (health care personnel) inspect the parameter data in a correlated period which are comparatively displayed in the first part 224 and the second part 226, so as to comprehensively analyze the conditions of the patient. Likewise, there are also two or more floating windows to comparatively display various types of historical data in one and the same monitoring period. Of course, more than two floating windows may comparatively display multiple types of historical data. These floating windows may be arranged in the display region of the display in a superposed or tiled manner, which is more convenient for the user to compare and inspect the parameter data of the patient.

Figure 4:
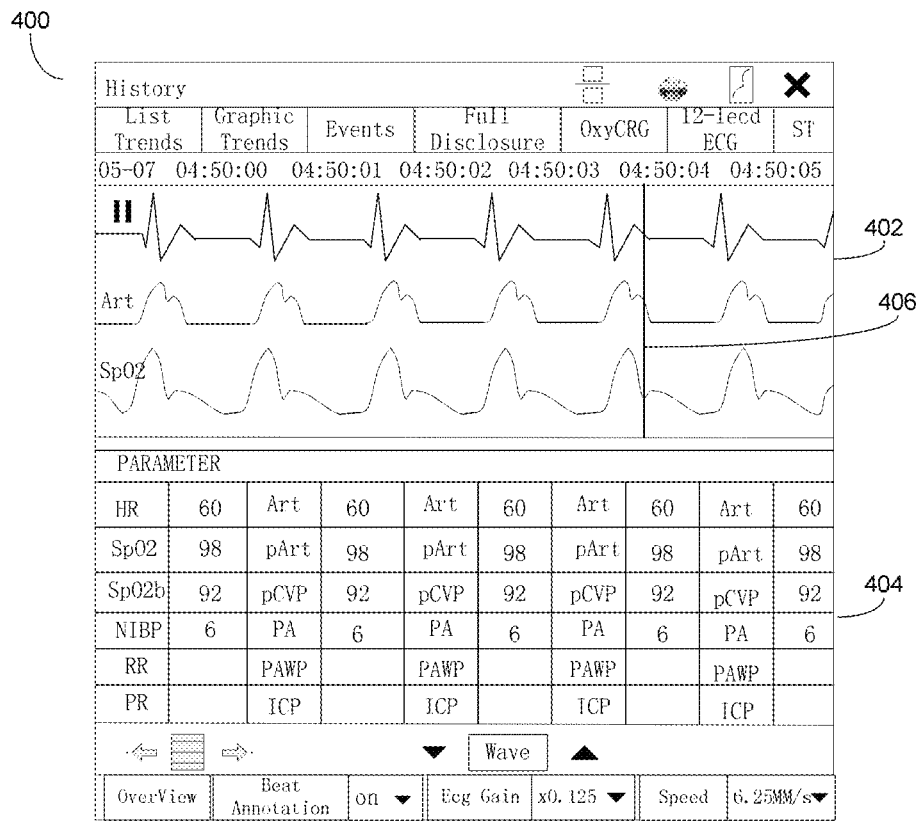
FIG. 4 is a schematic diagram of a GUI of a historical monitoring time interval of a medical monitoring system according to some embodiments.

FIG. 4 is a schematic diagram of a GUI 400 where historical data is displayed in a waveform display region 402 and a numerical value display region 404. The user may touch the waveform displayed in the waveform display region 402 to select a time point, after which the numerical values of corresponding parameters may be displayed in the numerical value display region 404. In addition, a line 406 corresponding to a selected time point may be displayed in the waveform display region 402.

FIG. 5 is a schematic diagram of a GUI 500 where parameter data is displayed in the form of a list trend of some embodiments of the present disclosure. In some embodiments, the list trend describes various parameters in the form of numerical values. In some embodiments, in the form of the list trend, a time frame 502 labels selected time point.

Figure 6:
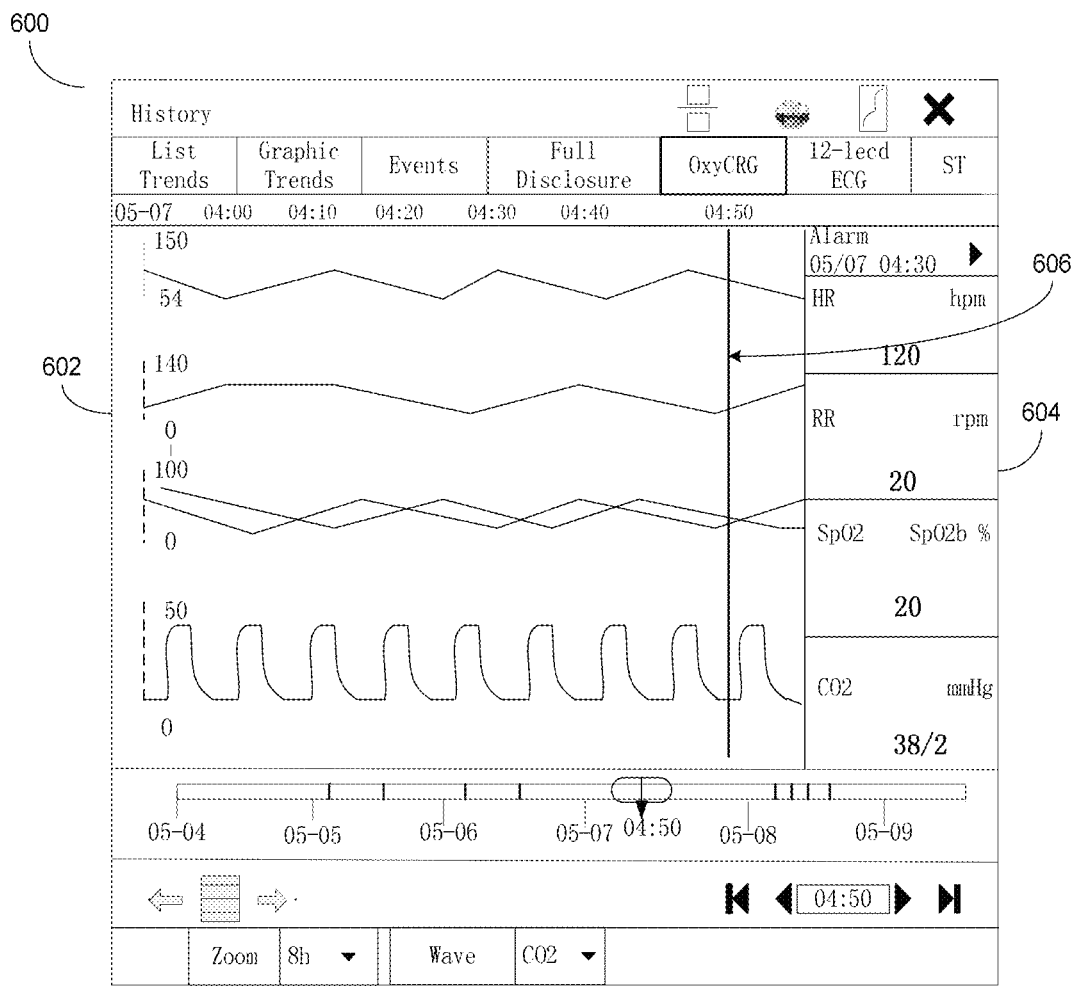
FIG. 6 is a schematic diagram of a GUI of a historical monitoring time interval of a medical monitoring system according to some embodiments.

FIG. 6 is a schematic diagram of a GUI 600 where parameter data relates to respiratory oxygenation. In some embodiments, the mode includes a waveform display region 602 and a numerical value display region 604. The user may touch the waveform displayed in the waveform display region 602 to select a time point, after which the numerical values of corresponding parameters may be displayed in the numerical value display region 604. In addition, a line 606 corresponds to selected time point may be displayed in the waveform display region 602.

Figure 7:
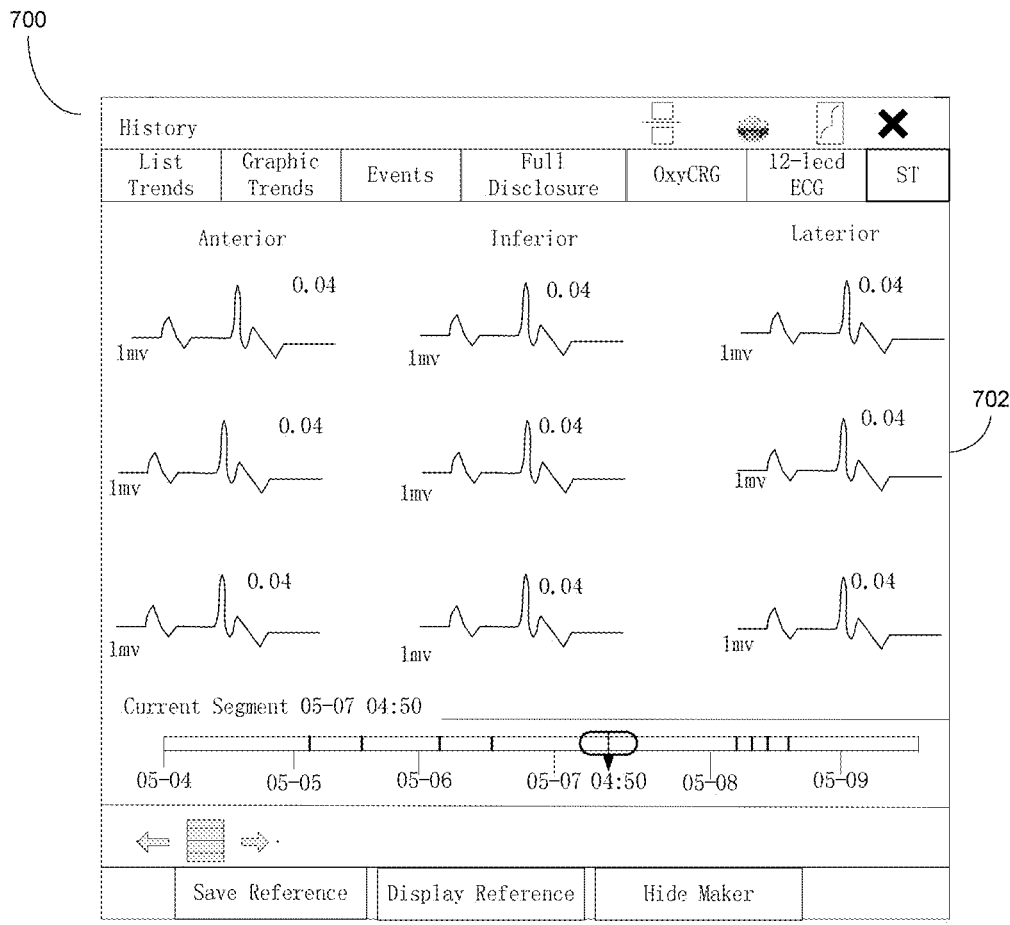
FIG. 7 is a schematic diagram of a GUI of a historical monitoring time interval of a medical monitoring system according to some embodiments.

FIG. 7 is a schematic diagram of a GUI 700 where parameter data is displayed in the type of an ST segment. In some embodiments, an ST segment displays a change in the ST segment in a waveform display region 702.

In some embodiments, the display region of the display may be further divided into a plurality of regions, the number of the plurality of regions being at least three, including a first region, a second region, and a third region, where the first region, the second region and the third region may be arranged in a tiled manner.

In some embodiments, the first region, the second region and the third region respectively and correspondingly display current parameter data, a first type of data and a second type of data. In the historical monitoring period, when the first type of data displayed in the second region and the second type of data displayed in the third region are updated according to selected inspecting period respectively. In this embodiment, the first type of data and the second type of data are any two of a holographic waveform, a parameter graphic trend, a list trend, an anomalous event, respiratory oxygenation, a 12-ECG and an ST segment. In some embodiments, a timeline is displayed in the second region or the third region. An inspecting label is displayed on the timeline, and the monitoring period is selected by moving the inspecting label.

Figure 8:
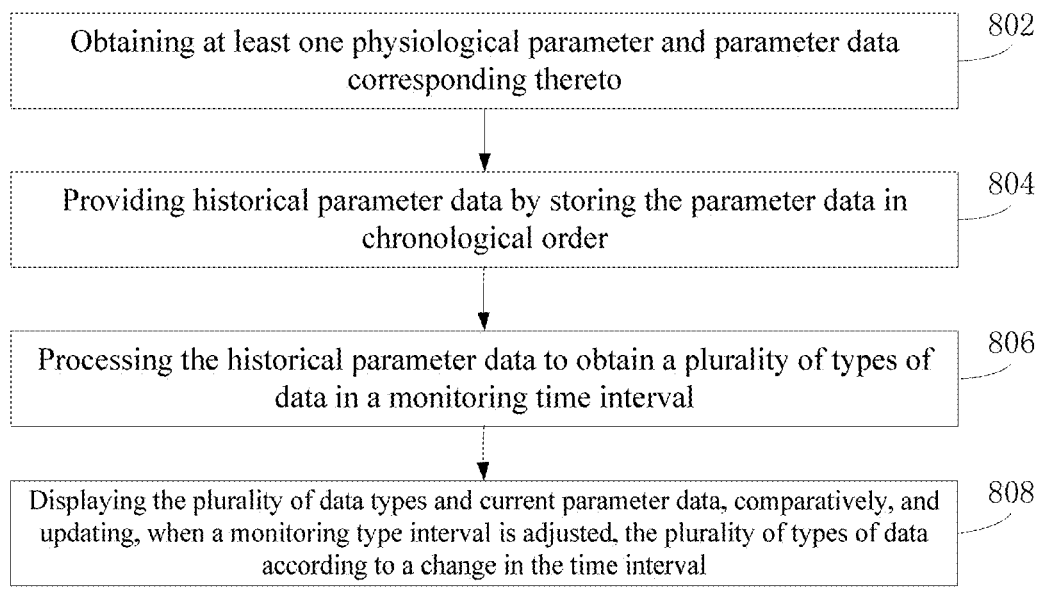
FIG. 8 is a flowchart of a method of displaying monitoring data according to some embodiments.

As shown in FIG. 8, a method of displaying monitoring data in some embodiments of the present disclosure may include:

Step 802, obtaining at least one physiological parameter and parameter data corresponding thereto;

Step 804, providing historical parameter data by storing the parameter data in a chronological order;

Step 806, processing the historical parameter data to obtain various types of historical data in one and the same monitoring period; and Step 808, displaying the various types of historical data and the current parameter data, comparatively, and updating, when a inspecting period is adjusted, the various types of historical data according to a change in the inspecting period.

Specific implementations of step 802, step 804, step 806 and step 808 are described with reference to FIGS. 4-7 above.

Figure 9:
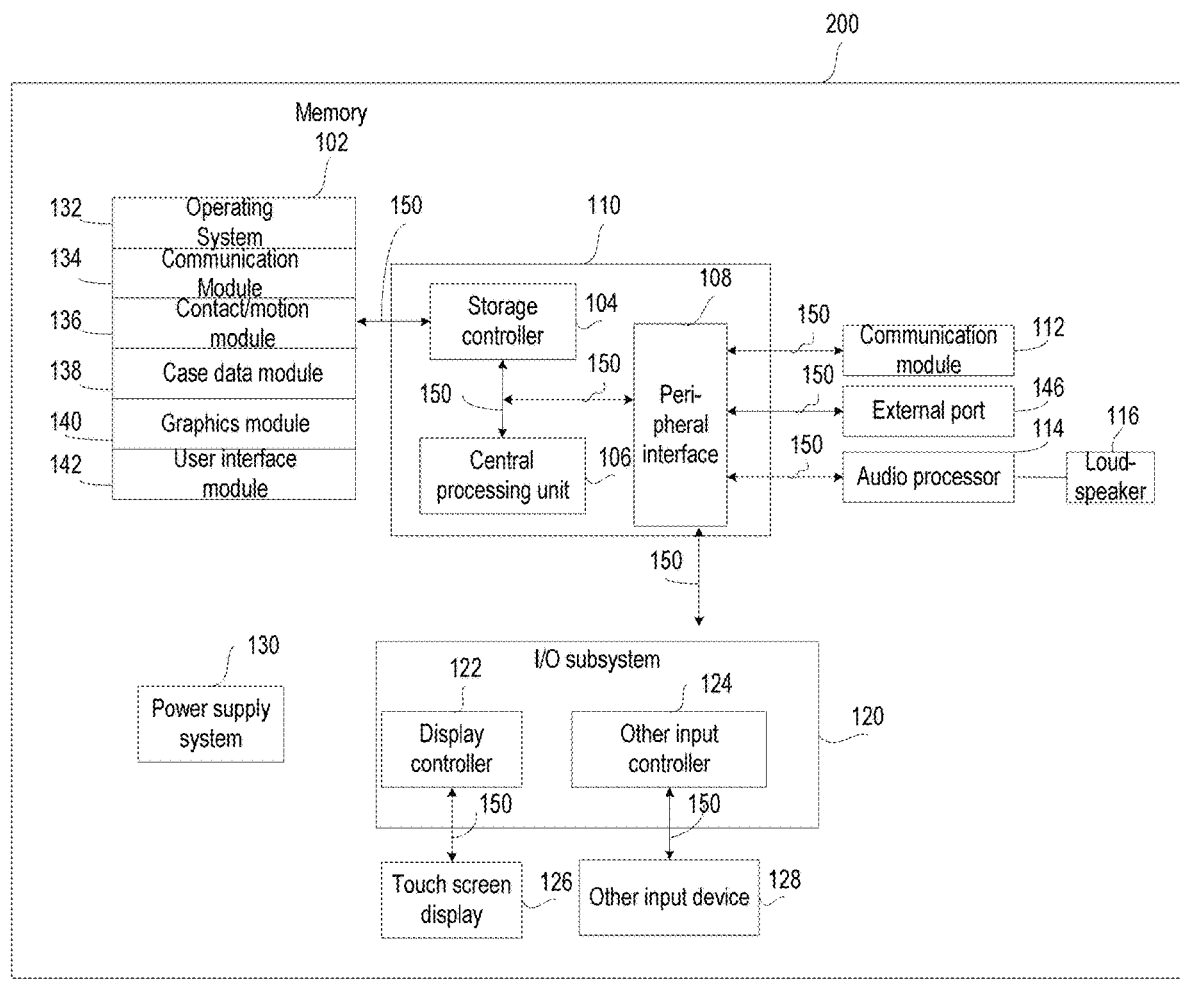
FIG. 9 is a structural block diagram of a monitoring data display device according to some embodiments.

As shown in FIG. 9, the monitoring data display device 200 in some embodiments of the present disclosure may include a memory 102 including one or more computer readable storage mediums, a storage controller 104, a central processing unit 106 (which may include one or more processors and/or controllers), a peripheral interface 108, an I/O subsystem 120, a display controller 122, a touch display screen 126, other input apparatus controller 124, and other input apparatus 128. The monitoring system 100 may further include a communication module 112, an audio processor 114, a loudspeaker 116, a signal sampling device 200, an external port 146 and a power supply system 130 (comprising a DC/DC conversion circuit and/or an AC/DC conversion circuit). The above various elements or modules may intercommunicate on one or more communication buses or signal lines 150.

The various parts of the monitoring data display device 200 may be similar to the parts of the medical monitoring system 100 heretofore described. The specific display method of the GUI of the monitoring data display device 200 may refer to the description of the GUI in FIGS. 4-7.

The medical monitoring system, method of displaying monitoring data, and monitoring data display device enhance convenience for users (health care personnel) to inspect parameter data of a patient in a historical monitoring period, greatly improving the user experience.

The above-mentioned examples merely represent several embodiments, giving specifics and details thereof, but should not be understood as limiting the scope of the present patent of disclosure thereby. It should be noted that a person of ordinary skill in the art may also make some alterations and improvements without departing from the spirit of the present disclosure and these would all fall within the scope of protection of the present disclosure. Therefore, the scope of protection of the present patent of disclosure shall be in accordance with the appended claims.

What is claimed is:

1. A medical monitoring system, comprising:
a memory that stores historical parameter data for a patient obtained from at least two different signal sampling devices, the historical parameter data corresponding to at least two respective physiological parameters of the patient;
a processor that retrieves from the memory the patient's historical parameter data of at least two different types corresponding to the at least two different signal sampling devices for a specified time interval;
a display controller that continuously displays in a monitoring time interval current physiological parameters for the patient in a first area of a graphical user interface on a display screen and comparatively displays in a historical monitoring time interval at least a portion of the patient's historical parameter data of each of the at least two types in at least two different respective areas of the graphical user interface;
wherein, in response a new historical monitoring time interval being specified, the processor retrieves from the memory the patient's historical parameter data of the at least two different types for the new specified historical monitoring time interval, and wherein the display controller comparatively displays at least a portion of the patient's historical parameter data of each of the at least two types for the new specified historical monitoring time interval in the at least two different respective areas of the graphical user interface.

2. The medial monitoring system of claim 1, wherein the at least two types of parameter data comprise at least two of full-disclosure holographic waveform, parameter graphic trend, list trend, anomalous events, respiratory oxygenation, 12-lead ECG, ST segment, and overview.

3. The medical monitoring system of claim 1, wherein each of the respective areas is a floating window within the graphical user interface.

4. The medical monitoring system of claim 1, wherein the number of display areas is at least three, and wherein one display area displays current parameter data, and the other two display areas comparatively display the at least two types of parameter data for the specified time interval.

5. The medical monitoring system of claim 4, wherein the at least two types of parameter data comprise a first type of parameter data and a second type of parameter data, and the display areas comprise a first area, a second area, and a third area, with the first area, the second area and the third area respectively displaying the current parameter data, parameter data of the first type, and parameter data of the second type; and
wherein, when the parameter data of the first type displayed in the second area changes with time over a monitoring time interval, the parameter data of the second type being comparatively displayed in the third area are updated accordingly.

6. The medical monitoring system of claim 5, wherein the first type of parameter data and the second type of parameter data are any two of full-disclosure holographic waveform, parameter graphic trend, list trend, anomalous events, respiratory oxygenation, 12-lead ECG, ST segment, and overview.

7. The medical monitoring system of claim 5, wherein a timeline is displayed in at least one of the second area or the third area of the graphical user interface; and
wherein an inspecting label is displayed on or near the timeline, the inspecting label for changing the specified time interval in response to a user moving the inspecting label along the timeline.

8. The medical monitoring system of claim 7, wherein a time point corresponding to the inspecting label is displayed on the timeline; and
wherein the time point is displayed as a time window or a vertical timeline on the display areas which are comparatively displayed; and wherein, when the inspecting label is moved by a user, the time window or the vertical timeline moves accordingly.

9. The medical monitoring system of claim 4, wherein the second and third areas are arranged in parallel from top to bottom.

10. The medical monitoring system of claim 1, wherein the second and third areas are arranged in a tiled manner.

11. A method of displaying monitoring data, comprising:
obtaining historical parameter data for a patient from at least two different signal sampling devices, the historical parameter data corresponding to at least two respective physiological parameters of the patient;
storing the historical parameter data in a memory;
retrieving from the memory the patient's historical parameter data of at least two different types corresponding to the at least two different signal sampling devices for a specified time interval;
continuously displaying in a monitoring time interval current physiological parameters for the patient in a first area of a graphical user interface on a display screen;
comparatively displaying in a historical monitoring tme interval at least a portion of the patient's historical parameter data of each of the at least two types in at least two different respective areas of the graphical user interface;
retrieving from the memory, in response a new historical monitoring time interval being specified, the patient's historical parameter data of the at least two different types for the new specified historical monitoring time interval, and comparatively displaying at least a portion of the patient's historical parameter data of each of the at least two types for the new specified historical monitoring time interval in the at least two different respective areas of the graphical user interface.

12. The method of claim 11, wherein the at least two types of parameter data comprise at least two of full-disclosure holographic waveform, parameter graphic trend, list trend, anomalous events, respiratory oxygenation, 12-lead ECG, ST segment, and overview.

13. The method of claim 11, wherein each of the respective areas is a floating window within the graphical user interface.

14. The method of claim 11, wherein the number of display areas is at least three, and wherein one display area displays current parameter data, and the other two display areas comparatively display the at least two types of parameter data for the specified time interval.

15. The method of claim 14, wherein the at least two types of parameter data comprise a first type of parameter data and a second type of parameter data, and the display areas comprise a first area, a second area, and a third area, with the first area, the second area and the third area respectively displaying the current parameter data, parameter data of the first type, and parameter data of the second type; and
wherein, when the parameter data of the first type displayed in the second area changes with time over a monitoring time interval, the parameter data of the second type being comparatively displayed in the third area are updated accordingly.

16. The method of claim 14, wherein the first type of parameter data and the second type of parameter data are any two of full-disclosure holographic waveform, parameter graphic trend, list trend, anomalous events, respiratory oxygenation, 12-lead ECG, ST segment, and overview.

17. The method of claim 14, further comprising:
displaying a timeline in at least one of the second area or the third area of the graphical user interface; and
displaying an inspecting label on or near the timeline, the inspecting for changing the specified time interval in response to a user moving the inspecting label along the timeline.

18. The method of claim 17, further comprising:
displaying a time point corresponding to the inspecting label on the timeline;
wherein the time point is displayed as a time window or a vertical timeline on the display areas which are comparatively displayed; and
wherein, when the inspecting label is moved by a user, the time window or the vertical timeline moves accordingly.

19. The method of claim 14, further comprising arranging the second and third areas in parallel from top to bottom.

20. A non-transitory medium comprising program code that, when executed by a processor, cause the processor to perform a method of displaying monitoring data, the method comprising:
obtaining historical parameter data for a patient from at least two different signal sampling devices, the historical parameter data corresponding to at least two respective physiological parameters of the patient;
storing the historical parameter data in a memory;
retrieving from the memory the patient's historical parameter data of at least two different types corresponding to the at least two different signal sampling devices for a specified time interval;
continuously displaying in a monitoring time interval current physiological parameters for the patient in a first area of a graphical user interface on a display screen;
comparatively displaying in a historical monitoring time interval at least a portion of the patient's historical parameter data of each of the at least two types in at least two different respective areas of the graphical user interface;
retrieving from the memory, in response a new historical monitoring time interval being specified, the patient's historical parameter data of the at least two different types for the new specified historical monitoring time interval, and comparatively displaying at least a portion of the patient's historical parameter data of each of the at least two types for the new specified historical monitoring time interval in the at least two different respective areas of the graphical user interface.

* * * * *